United States Patent
Nazim et al.

(10) Patent No.: US 11,523,873 B2
(45) Date of Patent: Dec. 13, 2022

(54) CATHETER CONTROL MECHANISM WITH MAGNETIC RESONANCE IMAGING-COMPATIBLE TORQUE

(71) Applicant: Memorial Sloan-Kettering Cancer Center, New York, NY (US)

(72) Inventors: Kamran Nazim, Bronx, NY (US); Maribel Vazquez, New York, NY (US); Joanne Lee, Flushing, NY (US); Estefany Condo, Great Neck, NY (US); Luis Cardoso, New York, NY (US); Stephen Solomon, New York, NY (US); Govindarajan Srimathveeravalli, Kew Gardens, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 668 days.

(21) Appl. No.: 15/570,589

(22) PCT Filed: May 2, 2016

(86) PCT No.: PCT/US2016/030428
§ 371 (c)(1),
(2) Date: Oct. 30, 2017

(87) PCT Pub. No.: WO2016/176683
PCT Pub. Date: Nov. 3, 2016

(65) Prior Publication Data
US 2018/0132954 A1 May 17, 2018

Related U.S. Application Data

(60) Provisional application No. 62/155,205, filed on Apr. 30, 2015.

(51) Int. Cl.
*A61B 34/35* (2016.01)
*A61B 34/30* (2016.01)
(Continued)

(52) U.S. Cl.
CPC .............. *A61B 34/35* (2016.02); *A61B 5/055* (2013.01); *A61B 34/30* (2016.02);
(Continued)

(58) Field of Classification Search
CPC ......... A61B 34/35; A61B 34/30; A61B 5/055; A61B 2034/301; A61M 25/0147
(Continued)

(56) References Cited

U.S. PATENT DOCUMENTS

2009/0326354 A1* 12/2009 Mao .................... A61B 5/14532
600/344
2009/0326364 A1 12/2009 Goldenberg et al.
(Continued)

FOREIGN PATENT DOCUMENTS

WO 2014/156221 A1 10/2014

*Primary Examiner* — Phillip A Gray
(74) *Attorney, Agent, or Firm* — Hunton Andrews Kurth LLP

(57) ABSTRACT

Exemplary embodiments of the present disclosure can include for example, an apparatus, which can include a manipulating arrangement configured to cause a medical device to move, where a portion of the manipulating arrangement can be partly composed of a non-magnetic material, and a computer arrangement in a communication with the manipulating arrangement, and configured to remotely operate the manipulating arrangement. The computer arrangement can include a computer. The communication can be a wired or wireless communication. The medical device can include (i) a catheter, (ii) an endoscope, or (iii) a needle. The manipulating arrangement can include a catheter as the medical device that can be attached to a manipulator.

19 Claims, 8 Drawing Sheets

(51) Int. Cl.
*A61B 5/055* (2006.01)
*A61M 25/01* (2006.01)
*A61B 17/00* (2006.01)

(52) U.S. Cl.
CPC ............... *A61M 25/0147* (2013.01); *A61B 2017/00911* (2013.01); *A61B 2034/301* (2016.02)

(58) Field of Classification Search
USPC .................................................. 604/510
See application file for complete search history.

(56) References Cited

U.S. PATENT DOCUMENTS

| | | | |
|---|---|---|---|
| 2010/0063630 A1* | 3/2010 | Sutherland | A61B 90/25 700/264 |
| 2011/0071347 A1* | 3/2011 | Rogers | A61B 1/00149 600/104 |
| 2013/0218005 A1* | 8/2013 | Desai | A61B 5/062 600/424 |
| 2013/0296737 A1* | 11/2013 | McMillan | A61B 10/02 600/562 |
| 2014/0058406 A1* | 2/2014 | Tsekos | A61B 34/30 606/130 |

* cited by examiner

CATHETER CONTROL MECHANISM WITH MAGNETIC RESONANCE IMAGING-COMPATIBLE TORQUE

CROSS-REFERENCE TO RELATED APPLICATION(S)

This application relates to and claims the benefit and priority from International Patent Application No. PCT/US2016/030428 filed on May 2, 2016, which claims the benefit and priority from U.S. Provisional Patent Application No. 62/155,205, filed on Apr. 30, 2015, the entire disclosures of which is are incorporated herein by reference.

FIELD OF THE DISCLOSURE

The present disclosure relates generally to a control of a catheter, and more specifically, to exemplary embodiments of an exemplary catheter control mechanism with magnetic resonance imaging-compatible torque.

BACKGROUND INFORMATION

In magnetic resonance imaging ("MRI"), physicians can be exposed to radiation from x-rays, or other types of radiation, while operating a medical device (e.g., a catheter) during the imaging process. For example, invasive cardiologists and angiologists are exposed to long-term, low-dose occupational radiation while operating the catheter during a MRI. While efforts have been made to limit the radiation dose to a patient, less attention has been paid to factors that can affect the operator radiation dose and how to minimize the operator radiation dose.

Thus, it may be beneficial to provide an exemplary catheter control mechanism with magnetic resonance imaging-compatible torque, which can decrease and/or limit a radiation dose that a physician can be exposed to.

SUMMARY OF EXEMPLARY EMBODIMENTS

To that end, an apparatus according to certain exemplary embodiments of the present disclosure can be provided, which can include a manipulating arrangement configured to cause a medical device to move, where a portion of the manipulating arrangement can be partly composed of a non-magnetic material, and a computer arrangement in a communication with the manipulating arrangement, and configured to remotely operate the manipulating arrangement. The computer arrangement can include a computer. The communication can be a wired or wireless communication. The medical device can include (i) a catheter, (ii) an endoscope, or (iii) a needle. The manipulating arrangement can include a catheter as the medical device that can be attached to a manipulator.

In some exemplary embodiments of the present disclosure the manipulator can include a plurality of actuators, and where the computer arrangement can be configured to manipulate the actuators to cause the catheter to move. The manipulator can further include a plurality of wires connected to the actuators and a plurality of springs, through a plurality of pulleys. One of the wires can be connected to one of the actuators at a first end, and to one of the springs at a second end, through at least one of the pulleys. The springs and the catheter can be connected to a rod.

In certain exemplary embodiments of the present disclosure, a movement of the actuators in a first direction can cause a movement of the catheter in a second direction, where the second direction can be different than the first direction. The manipulator can include a plurality of gears configured to cause a rotary motion of the manipulator, where the gears can be bevel gears. The manipulator can further include a rack that can be configured to drive the gears. The manipulator can also further include a plurality of bearings configured to provide a relatively frictionless motion of the gears. The manipulating arrangement can be located at or near a magnetic resonance imaging (MRI) apparatus in a MRI room, and the computer hardware arrangement can be located in a location that can be outside of the MRI room.

According to another exemplary embodiment of the present disclosure, a method can be provided for manipulating a catheter, which can include, for example, attaching a catheter to a catheter manipulating arrangement, providing the catheter manipulating arrangement at or near a magnetic resonance imaging (MRI) apparatus in a MRI room, and remotely controlling the catheter manipulating arrangement outside of the MRI room. The catheter manipulating arrangement can includes a plurality of actuators, a plurality of wires connected to the actuators at a first end and a plurality of springs at a second end, through a plurality of pulleys, and at least one rod connected to the springs. One of the wires can be connected to one of the actuators and to one of the springs, through one of the pulleys. The remotely controlling of the catheter manipulating arrangement can include causing a movement of the actuators in a first direction, which can cause a movement of the at least one rod in a second direction, where the second direction can be different than the first direction.

In a further exemplary embodiment of the present disclosure, an apparatus can be provided, which can include an actuator, a manipulator coupled to the actuator, a medical device attached to the manipulator, and a computer arrangement in a communication with the actuator, and configured to cause a movement of the actuator, that can cause a movement in the medical device.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1:
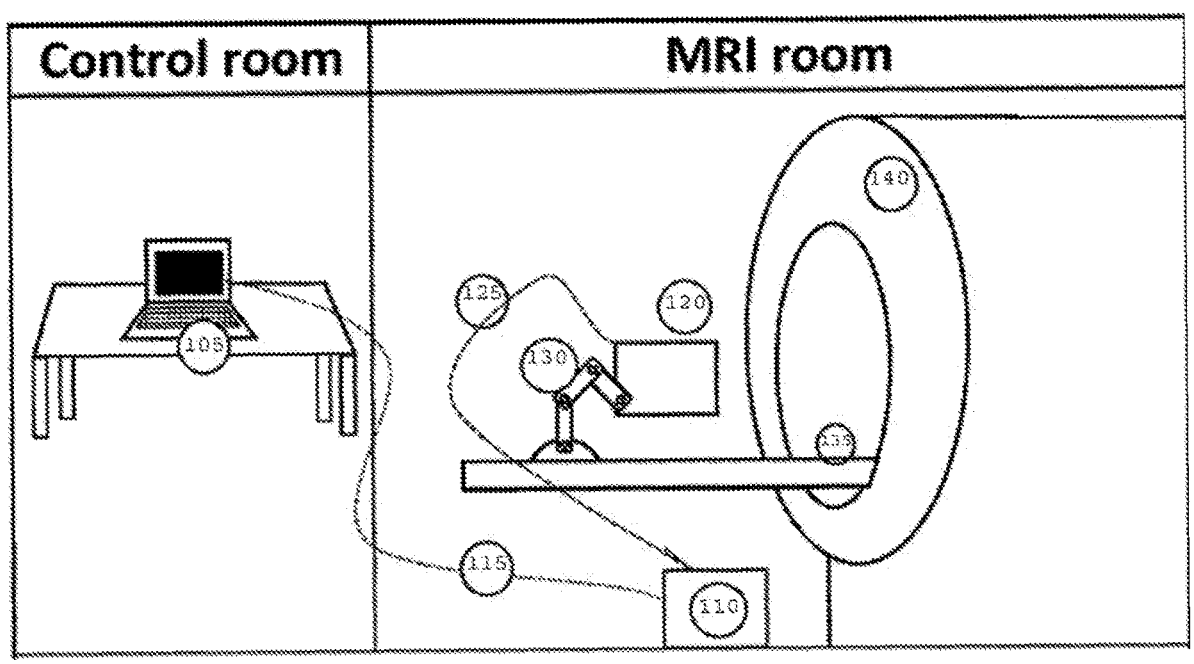
FIG. 1 is a diagram of a control room and a MRI room according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary system/apparatus, according to an exemplary embodiment of the present disclosure, can be used to reduce a physicians' exposure to radiation (e.g., from x-rays, etc.), as well as increase soft tissue imaging quality by utilizing a catheter control mechanism that can be used on conjunction with a magnetic resonance imaging ("MRI") apparatus. For example, the exemplary system/apparatus can safely torque and/or advance a catheter (e.g., via a remote operation) for various medical interventions, including cardiac applications.

For example, the exemplary MRI-compatible catheter control system, according to an exemplary embodiment of the present disclosure, can be used to reduce and/or minimize image quality degradation, for example, by separating the actuators from the manipulators in the exemplary catheter control system/apparatus. The exemplary system/apparatus can be used to drive or otherwise control any flexible elongate device (e.g., needles, catheters and/or endoscopes). Actuators can be separated from the manipulating arms, which can facilitate the use of, non-magnetic resonance ("MR") safe actuators to drive a completely MR-safe robotic system. Linear actuators and flexible transmission system can be used to transmit power over any suitable distance. Translation of motion can be achieved using, for example, non-magnetic mechanical transmission elements.

Figure 2:
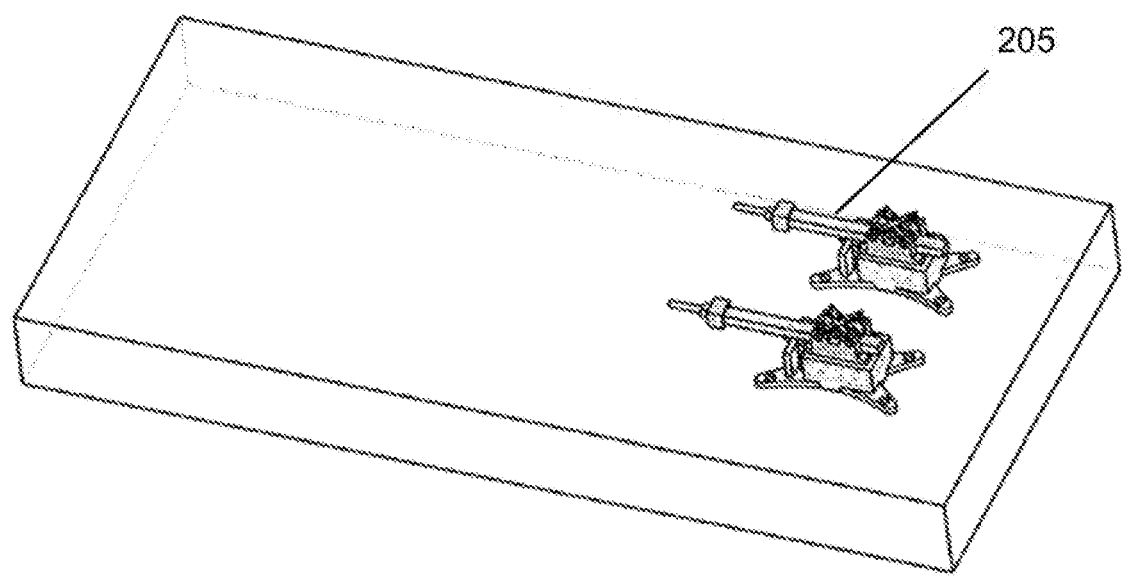
FIG. 2 is a diagram of exemplary actuators according to an exemplary embodiment of the present disclosure.

FIG. 1 shows an exemplary diagram of a control room connected to a MRI room, according to an exemplary embodiment of the present disclosure. One or more computers, for example, a computing device 105 (e.g., which can be or include a desktop or laptop computer) can be located in the control room, and can be connected to the exemplary manipulator (e.g., to an actuator box 110 located in the MRI room), using for example, cables 115. Thus, for example, a physician can operate the exemplary manipulator outside of the MRI room, and can be safe from the radiation present within the room. Additionally, or alternatively, the computer or computing device 105 can be connected to actuator box 110 through a wireless communication (e.g., RF, Wi-Fi, Bluetooth or any other suitable wireless connection). Actuators can be connected to the manipulator box 120 using, for example, wires 125 (e.g., which can be flexible transmission wires). An exemplary mounting arm 130 can be placed on top of the patient bed 135, and can hold the manipulator box as the system moves into and out of the MRI machine 140. FIG. 2 shows an exemplary diagram of an exemplary actuator 205 that can be used in conjunction with the exemplary system/apparatus, according to an exemplary embodiment of the present disclosure.

Figure 3:
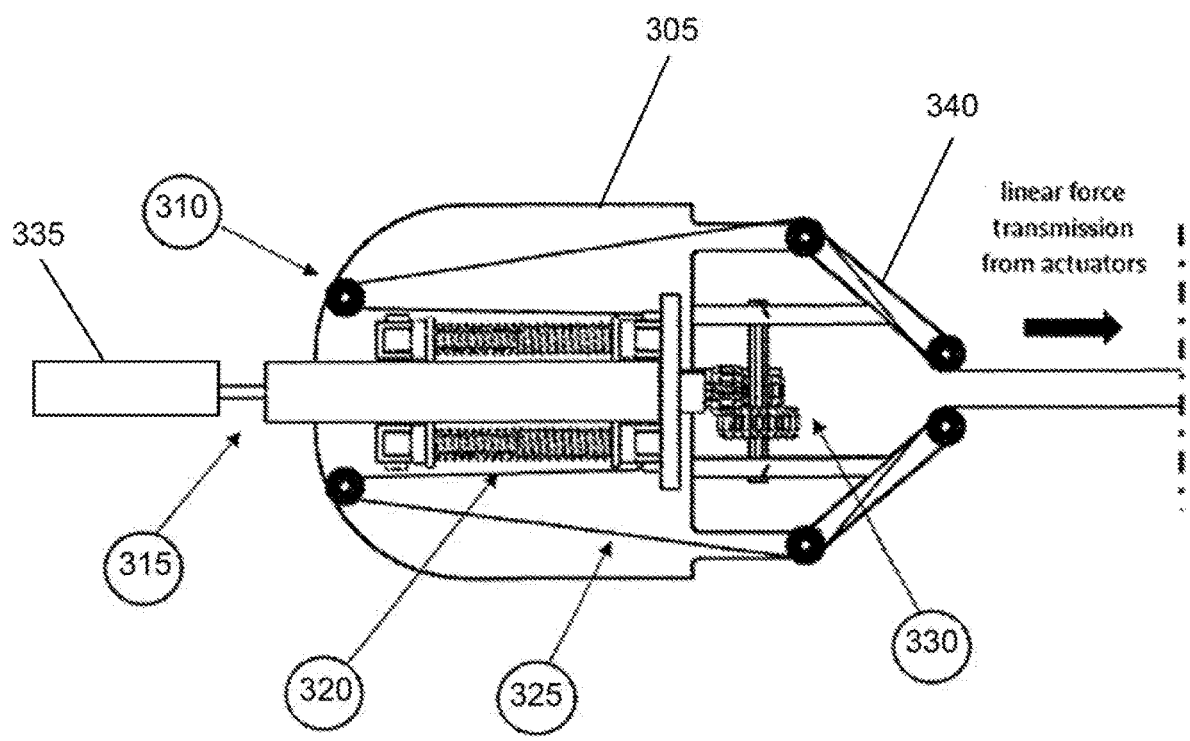
FIG. 3 is a diagram of a top view an exemplary manipulator arrangement according to an exemplary embodiment of the present disclosure.

FIG. 3 shows an exemplary diagram of a top view of the exemplary manipulator arrangement 305, according to an exemplary embodiment of the present disclosure. For example, the exemplary manipulator arrangement 305 can include one or more pulleys 310, a rod 315, to which a catheter 335 can be attached, and one or more springs 320 encased in a piston that can drive the linear motion forward. Flexible transmission wires 325 can be pulled by the actuators 340 such that the transmitted pulled force can compress the springs 320, and drive the catheter 335 forward. A set of bevel gears 330 can drive the rotary motion (e.g., up down motion) of the exemplary manipulator arrangement 305.

Figure 4:
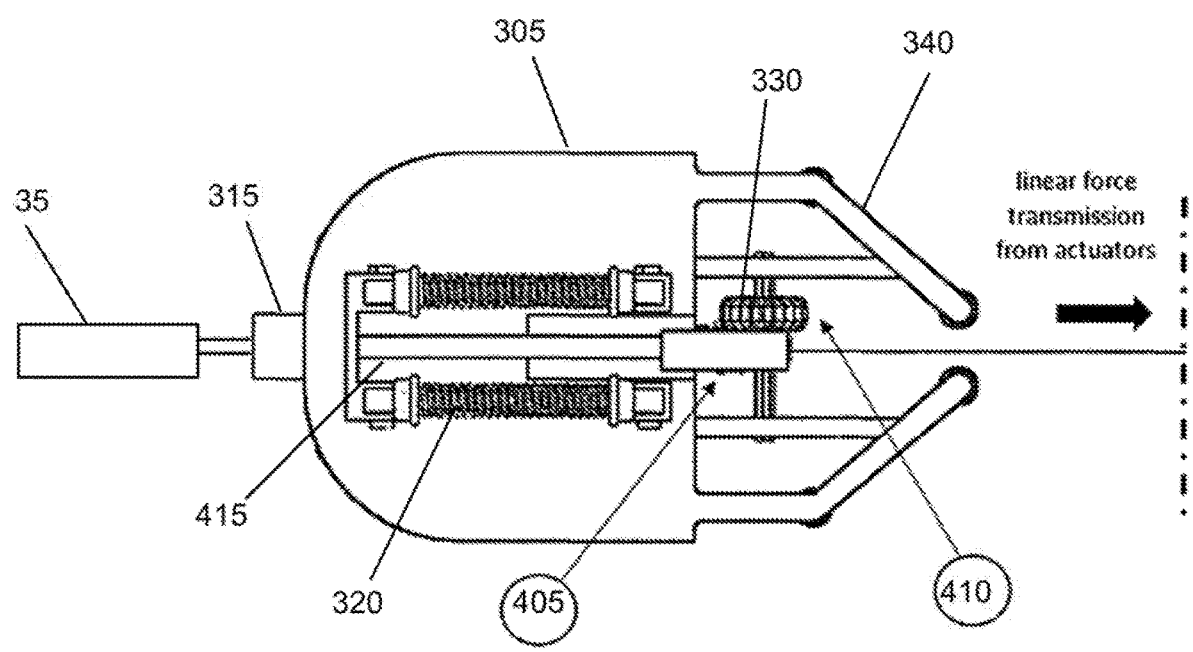
FIG. 4 is a diagram of a bottom view of the exemplary manipulator arrangement according to an exemplary embodiment of the present disclosure.

FIG. 4 shows an exemplary diagram of a bottom view of the exemplary manipulator arrangement 305, according to an exemplary embodiment of the present disclosure. A rack 405 can be used to drive one or more bevel gears 410, which can be used to maintain tension. Wires 415 can be used for rotary motion of the exemplary bevel gears 410.

Figure 5:
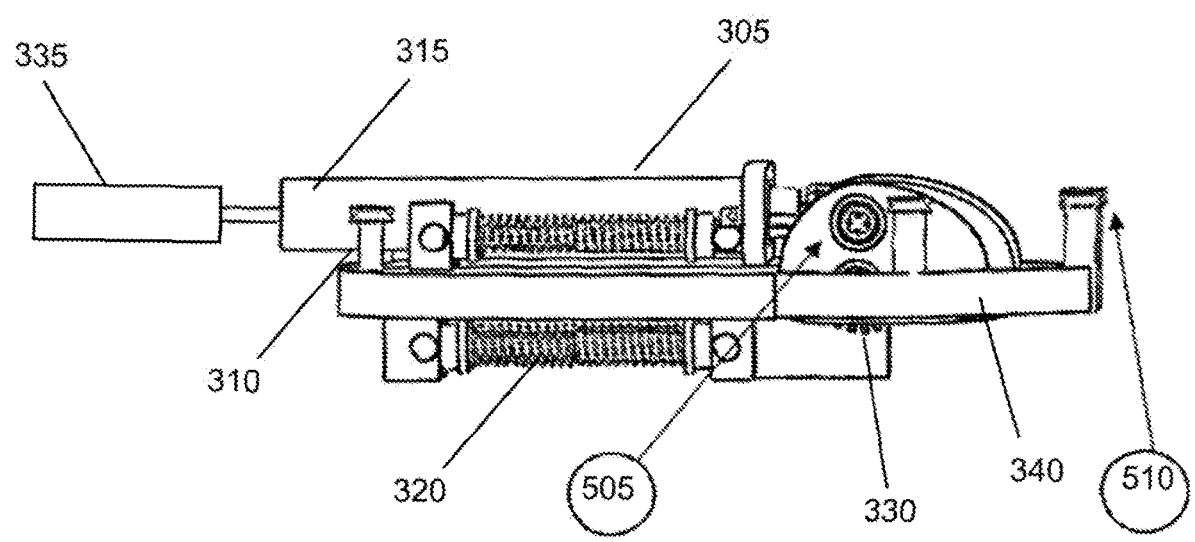
FIG. 5 is a diagram of a side view of the exemplary manipulator arrangement according to an exemplary embodiment of the present disclosure.

FIG. 5 shows an exemplary diagram of a side view of the exemplary manipulator arrangement 305, according to an exemplary embodiment of the present disclosure. One or more bearing 505 can provide relatively frictionless rotation of bevel gear pulleys 510.

Figure 6:
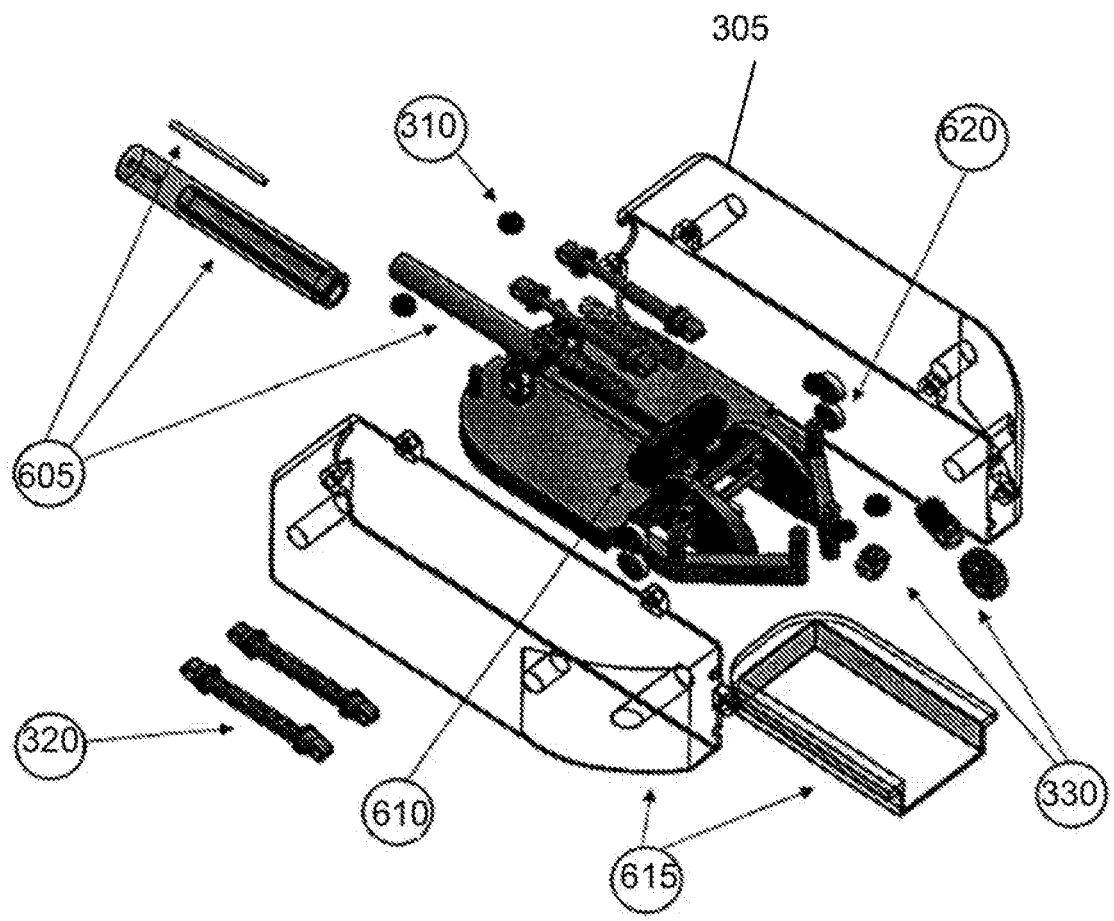
FIG. 6 is a diagram of an exploded view of the exemplary manipulator arrangement according to an exemplary embodiment of the present disclosure in a disassembled configuration.

FIG. 6 shows an exemplary diagram of an exploded view of the exemplary manipulator arrangement 305, according to an exemplary embodiment of the present disclosure. For example, the diagram of FIG. 6 illustrates the pulleys 310, and rods 605, attached to the catheter springs 320 and an attachment mechanism 610, which facilitate the linear motion of the pistons. Encasing 615 or other housings can be used to encase various components of the exemplary manipulator arrangement 305. The diagram provided in FIG. 6 also shows the bevel gears 330 and frictionless bearings 620.

The exemplary manipulator, according to an exemplary embodiment of the present disclosure, can be the part of the system that is located at or near a MR bed, and can translate the motor motions from the actuator part of the system. The exemplary actuator and manipulator can be connected by flexible and/or non-magnetic lines that can mechanically transmit linear motion. For example, all or some of components in the manipulator can be non-magnetic, using materials such as, for example, nylon and acrylic.

An exemplary system of gears and pulleys can be used to manipulate the linear motion into amplified linear motion of the catheter, as well as rotary motion. A pulling motion from the actuator can convert into a pushing motion on the catheter. Springs can be used to provide tension along the lines that can pull the catheter back as the actuator moves forward. The rotary motion can span a full 360 degree of motion.

Figure 7:
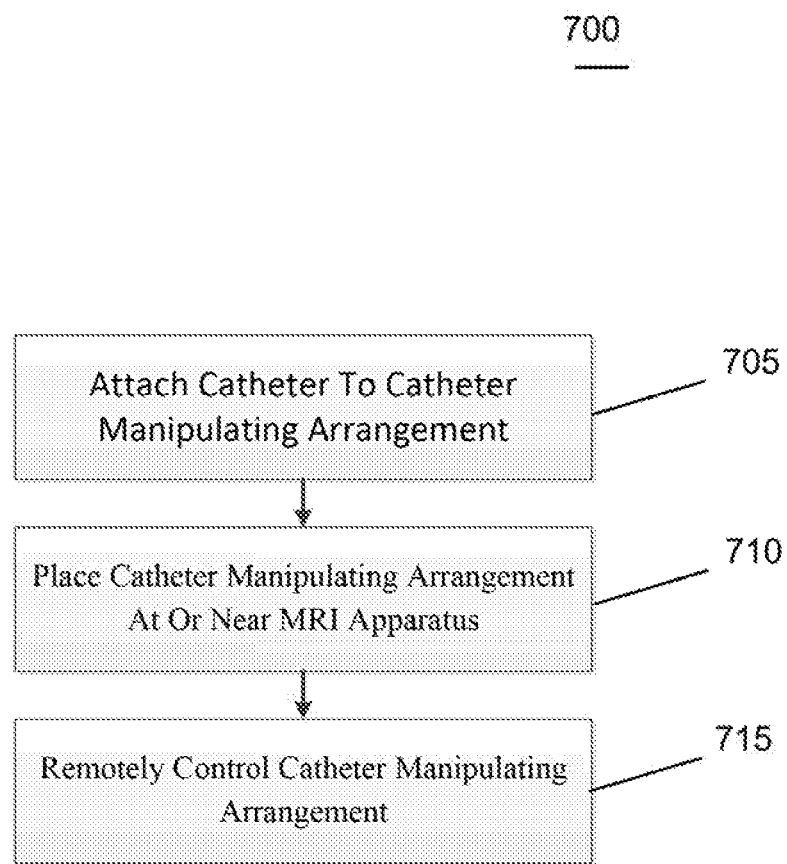
FIG. 7 is a flow chart of an exemplary method for manipulating a catheter according to an exemplary embodiment of the present disclosure.

FIG. 7 is a diagram of an exemplary method 700 for manipulating a catheter according to an exemplary embodiment of the present disclosure. For example, at procedure 705, a catheter can be attached to a manipulating arrangement, which can be remotely controlled by a physician. This exemplary procedure facilitates control of the catheter without exposing the physician to an unnecessary or undesired radiation. At procedure 710, the exemplary catheter manipulating arrangement, having the catheter attached thereto, is placed at or near a MRI apparatus in a MRI room. The MRI room can be shielded, which can limit exposure to radiation by any individual outside of the MRI room. At procedure 715, the physician can remotely control the catheter manipulating arrangement from another room (e.g., from a room that is different than the MRI room). The exemplary control of the catheter manipulating arrangement can include causing a movement of actuators in the catheter manipulating arrangement, which can cause a movement of the catheter. The catheter can be moved in a linear direction, or it can be rotated.

Figure 8:
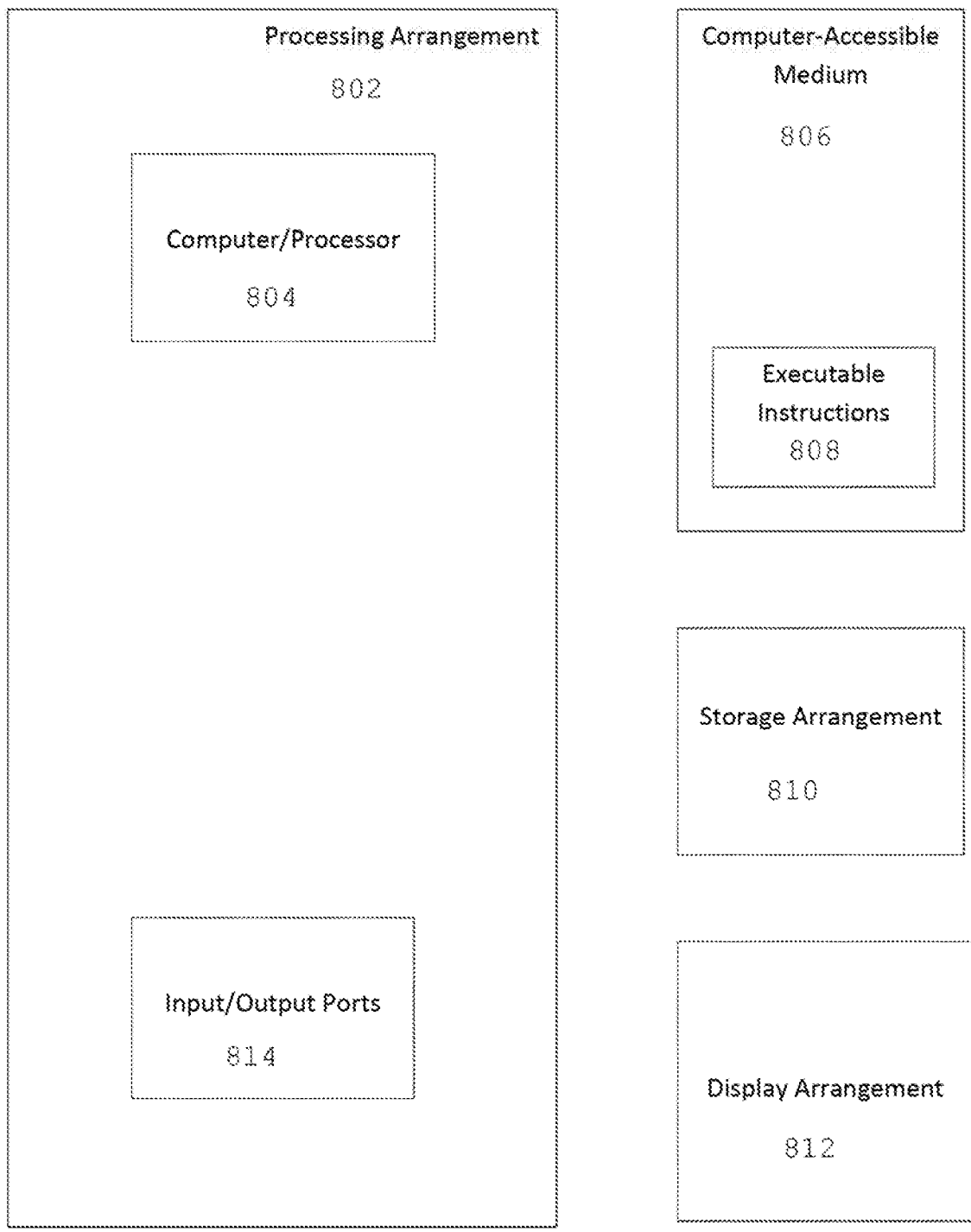
FIG. 8 is an illustration of an exemplary block diagram of an exemplary system in accordance with certain exemplary embodiments of the present disclosure.

FIG. 8 shows a block diagram of an exemplary embodiment of a system according to the present disclosure. For example, exemplary procedures in accordance with the present disclosure described herein can be performed by a processing arrangement and/or a computing arrangement 802. In addition, such exemplary system can be used to control of the exemplary manipulator arrangement 305, for example, via wireless communication. Such processing/computing arrangement 802 can be, for example entirely or a part of, or include, but not limited to, a computer/processor 804 that can include, for example one or more microprocessors, and use instructions stored on a computer-accessible medium (e.g., RAM, ROM, hard drive, or other storage device).

As shown in FIG. 8, for example a computer-accessible medium 806 (e.g., as described herein above, a storage device such as a hard disk, floppy disk, memory stick, CD-ROM, RAM, ROM, etc., or a collection thereof) can be provided (e.g., in communication with the processing arrangement 802), which can be used to communicate with and/or control the exemplary manipulator described herein above. The computer-accessible medium 806 can contain executable instructions 808 thereon. In addition or alternatively, a storage arrangement 810 can be provided separately from the computer-accessible medium 806, which can provide the instructions to the processing arrangement 802 so as to configure the processing arrangement to execute certain exemplary procedures, processes and methods, as described herein above, for example.

Further, the exemplary processing arrangement 802 can be provided with or include an input/output arrangement 814, which can include, for example a wired network, a wireless network, the internet, an intranet, a data collection probe, a sensor, etc. As shown in FIG. 8, the exemplary processing arrangement 802 can be in communication with an exemplary display arrangement 812, which, according to certain exemplary embodiments of the present disclosure, can be a touch-screen configured for inputting information to the processing arrangement in addition to outputting information from the processing arrangement, for example. Further, the exemplary display 812 and/or a storage arrangement 810 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. An apparatus comprising:
   a manipulating arrangement, comprising
      at least one actuator;
      at least one spring coupled to the at least one actuator; and
   a medical device connected to the at least one spring,
      wherein at least one portion of the manipulating arrangement is at least partly composed of a non-magnetic material, and
      wherein, in operation, a pulling movement of the at least one actuator in a first direction causes a pulling movement of the at least one spring and the medical device in a second direction, and wherein the second direction is different than the first direction; and
   a computer arrangement in a communication with the manipulating arrangement, and configured to remotely operate the manipulating arrangement.

2. The apparatus of claim 1, wherein the computer arrangement includes a computer.

3. The apparatus of claim 1, wherein the communication is a wired communication.

4. The apparatus of claim 1, wherein the communication is a wireless communication.

5. The apparatus of claim 4, wherein the medical device includes at least one of (i) a catheter, (ii) an endoscope, or (iii) a needle.

6. The apparatus of claim 1, wherein:
   (i) the at least one spring is coupled to the at least one actuator using at least one connector connected to the at least one actuator on a first end, and the at least one spring on a second end,
   (ii) the at least one spring includes a first spring and a second spring,
   (iii) the at least one connector includes a first connector and a second connector, and
   (iv) the at least one pulley includes at least one first pulley and at least one second pulley.

7. The apparatus of claim 6, wherein the first connector is connected to the first spring through the at least one first pulley and the second connector is connected to the second spring through the at least one second pulley.

8. The apparatus of claim 7, wherein the at least one first pulley includes three pulleys and the at least one second pulley includes three pulleys.

9. The apparatus of claim 1, wherein the at least one spring and the medical device are connected to one another using a rod.

10. The apparatus of claim 6, wherein the manipulating arrangement includes a plurality of gears configured to cause a rotary motion of the manipulating arrangement.

11. The apparatus of claim 10, wherein the gears are bevel gears.

12. The apparatus of claim 10, wherein the manipulating arrangement further includes a rack that is configured to drive the gears.

13. The apparatus of claim 10, wherein the manipulating arrangement further includes a plurality of bearings configured to provide a relatively frictionless motion of the gears.

14. The apparatus of claim 1, wherein the manipulating arrangement is located at or near a magnetic resonance imaging (MRI) apparatus in a MRI room, and wherein the computer hardware arrangement is boated in a location that is outside of the MRI room.

15. A method for manipulating a catheter comprising:
attaching a catheter to a catheter manipulating arrangement, wherein the catheter manipulating arrangement comprises:
 at least one actuator;
 at least one spring coupled to the at least one actuator; and
 a medical device connected to the at least one spring;
providing the catheter manipulating arrangement at or near a magnetic resonance imaging (MRI) apparatus in a MRI room; and
remotely controlling the catheter manipulating arrangement outside of the MRI room to cause a pulling movement of the at least one actuator in a first direction, which causes a pulling movement of the at least one spring and the medical device in a second direction, wherein the first direction, is different than the second direction.

16. The method of claim 15, wherein the catheter manipulating arrangement includes:
at least one rod connected to the at least one spring and the catheter.

17. The method of claim 16, wherein:
(i) the at least one spring is coupled to the at least one actuator using at least one connector connected to the at least one actuator on a first end, and the at least one spring on a second end,
(ii) the at least one spring includes a first spring and a second spring,
(iii) the at least one connector includes a first connector and a second connector, and
(iv) the at least one pulley includes at least one first pulley and at least one second pulley.

18. The method of claim 16, wherein the first connector is connected to the first spring through the at least one first pulley and the second connector is connected to the second spring through the at least one second pulley.

19. An apparatus comprising:
(a) a first actuating mechanism comprising:
 a first actuator, a first spring, and a first wire, wherein the first wire is connected to the first actuator and the first spring through at least one first pulley;
(b) a second actuating mechanism comprising:
 a second actuator, a second spring, and a second wire, wherein the second wire is connected to the second actuator and the second spring through at least one second pulley;
(c) a rod connected to the first actuating mechanism and the second actuating mechanism; and
(d) a medical device attached to the rod;
wherein, in operation, a pulling movement of the first and second actuators in a first direction causes a pulling movement of the first and second springs and the medical device in a second direction, and wherein the second direction is different than the first direction.

* * * * *